United States Patent [19]
Porter

[11] Patent Number: 5,458,896
[45] Date of Patent: Oct. 17, 1995

[54] TECHNIQUE FOR DETERMINING THE OXIDATIVE STATUS OF PACKAGED DRY OR INTERMEDIATE MOISTURE FOODS

[75] Inventor: William L. Porter, Natick, Mass.

[73] Assignee: The United States of America as represented by the Secretary of the Army, Washington, D.C.

[21] Appl. No.: 147,239

[22] Filed: Oct. 22, 1993

[51] Int. Cl.[6] ................................................. G01N 33/03
[52] U.S. Cl. ........................ 426/232; 426/87; 426/106; 426/126; 436/172; 436/165
[58] Field of Search ........................ 426/87, 106, 126, 426/231, 232; 436/60, 71, 165, 172

[56] References Cited

U.S. PATENT DOCUMENTS

| | | | |
|---|---|---|---|
| 3,343,663 | 9/1967 | Seidler | 426/126 |
| 3,556,816 | 1/1971 | Nughes | 426/16 |
| 4,241,129 | 12/1980 | Marton et al. | 428/126 |
| 4,253,848 | 3/1981 | Porter | 436/60 X |
| 4,257,776 | 3/1981 | Porter et al. | 436/60 |
| 4,310,578 | 1/1982 | Katsura et al. | 426/126 X |
| 4,861,632 | 8/1989 | Caggiano | 426/126 X |

OTHER PUBLICATIONS

Porter et al., "Use of polyomide oxidative fluorescence test on lipid emulsions: contrast in relative effectiveness of antioxidants in bulk versus dispersed systems", J. Agric. Food Chem., 37(3), 615–24, (1989).

Weist et al., "Development of a Fluorescence Sensor to Monitor Lipid Oxidation," J. Agric. Food Chem., vol. 40, No. 7, pp. 1158–1162, 1992.

Porter, abstract entitled "Polyamide Fluorescence as a Real Time, On–Line or In–Package, Sensor for Lipid Oxidation," Center for Advanced Food Technology Basic Research Conference, New Brunswick, N.J. Oct. 27, 1992.

Porter, abstract entitled "Polyamide Fluorescence as a Non–Destructive In–Package Test for Lipd Oxidation," Pittsburgh Conf. on Analytical and Applied Spectroscopy, Pittsburgh, Pa., Mar. 10, 1993.

*Primary Examiner*—Donald E. Czaja
*Assistant Examiner*—Milton I. Cano
*Attorney, Agent, or Firm*—John H. Lamming; Richard J. Donahue; Vincent J. Ranucci

[57] ABSTRACT

A non-destructive technique for examining the oxidative status of packaged, dry or intermediate moisture foods. In a preferred embodiment, the technique involves packaging the foods in an assembly comprising a container or pouch formed from a pair of sheets heat-sealed to one another along their peripheries. The sheets may each be a trilaminate comprising a polyethylene terephthalate outer layer, an aluminum foil middle layer and a polyolefin inner layer. One of the sheets is provided with a cut-out portion which serves as a light transmissive window. A device comprising a strip of polyethylene terephthalate which is coated on one side with a polyamide coating is mounted across the light transmissive window, with the polyamide coating facing in towards the interior of the pouch. The food within the pouch is stored within about 2 cm of the polyamide coating during oxidation. To test the oxidative status of the food, a beam of about 420 nm light is used to illuminate the polyamide coating through strip of polyethylene terephthalate, and the resultant fluorescence is observed through the strip of polyethylene terephthalate at a wavelength of approximately 464 nm.

10 Claims, 6 Drawing Sheets

TECHNIQUE FOR DETERMINING THE OXIDATIVE STATUS OF PACKAGED DRY OR INTERMEDIATE MOISTURE FOODS

The invention described herein may be manufactured, used and licensed by or for the Government for Governmental purposes without the payment to me of any royalty thereon.

BACKGROUND OF THE INVENTION

The present invention relates generally to techniques for determining the oxidative status of dry or intermediate moisture foods and more particularly to a novel technique for determining the oxidative status of packaged dry or intermediate moisture foods.

Lipids present in dry or intermediate moisture foods are susceptible to becoming rancid as a result of oxidation. This rancidity caused by oxidation is a major cause of food deterioration. The acceptability of a food product often depends on the extent to which such deterioration has occurred. Therefore, some technique for assessing the extent of oxidation arid for predicting remaining storage life is necessary. Sensory analysis is one of the most sensitive methods available. However, this method is obviously not practical for routine analysis. As a result, many chemical and physical techniques have been devised in an effort to quantify oxidative deterioration and to correlate the data with off-flavor development. Chemical methods include those which measure peroxide value, the thiobarbituric acid test, the Kreis test, those which measure total and volatile carbonyl compounds, and oxirane determination tests. Physical methods include ultraviolet and infrared spectroscopy, polarography, gas chromatography and refractometry. All of these methods, however, employ high temperature, or strong acid or solution, which classify such methods as destructive methods.

In U.S. Pat. No. 4,253,848 to Porter, which issued on Mar. 3, 1981 and which is incorporated herein by reference, there is disclosed a rapid, dry, room temperature, non-destructive method for assaying the oxidative status of unsaturated lipids in whole foods, fats or oils. Said method involves exposing dissolved or volatile compounds from oxidizing lipids to a plastic or glass strip coated on one side with a polyamide (poly-ε-caprolactam) coating and then observing a bluish-white fluorescence from the polyamide coating upon illumination with ultraviolet light. In accordance with the method disclosed in the aforementioned patent, illumination of the polyamide coating takes place from the direction of the exposed side of the polyamide coating, and observation of the resultant fluorescence typically takes place from the same side. Although some mention is made in the patent to applying the method disclosed therein to the inspection of packaged goods, the patent does not provide information as to how said inspection could be effected in an accurate and reproducible way and without requiring the opening of the package containing the goods.

SUMMARY OF THE INVENTION

It is an object of the present invention to provide a new and novel technique for determining the oxidative status of dry or intermediate moisture foods.

It is another object of the present invention to provide a technique as described above which permits the assaying of packaged dry or intermediate moisture foods without requiring the package containing the foods to be opened.

In furtherance of these and other objects, the present invention contemplates the use of a novel package assembly, the package assembly including a container or pouch for holding the food to be tested, the container or pouch having a light transmissive window or area. A glass or plastic strip which is coated on one side thereof with a polyamide coating is mounted over the light transmissive window, with the polyamide coating facing towards the inside of the container or pouch. A wire screen is preferably mounted over the coated strip to minimize contact between the polyamide coating and the food stored within the container. If, at the time of packaging the food within the container, the food is not positioned in sufficient proximity to the polyamide coating (i.e., within about 2 cm therefrom), the container must be shaken, inverted or otherwise disturbed so that the packaged food is brought into sufficient proximity to the polyamide coating during storage. To test the oxidative status of the packaged food, light of a suitable excitation wavelength is conducted from a light source external to the container through the light transmissive window and the glass or plastic strip to the polyamide coating. The resultant fluorescence emitted from the polyamide coating and transmitted through the glass or plastic strip and the light transmissive window is then observed at a location external to the container.

Preferably, the light used to excite the polyamide coating impinges upon the glass or plastic strip perpendicularly thereto, and the resultant fluorescence is observed at a shallow angle, e.g., approximately 22 degrees relative to the strip normal. If the strip is made of glass, the excitation wavelength is preferably either approximately 360 nm or approximately 420 nm, with a corresponding emission wavelength of approximately 430 nm or approximately 464 nm, respectively. If the strip is made of polyethylene terephthalate, an excitation wavelength of approximately 360 nm is not feasible as an excitation wavelength since polyethylene terephthalate strips exhibit their own contaminant fluorescence at approximately 410 when excited with light at approximately 360 nm. No such fluorescence is emitted from polyethylene terephthalate strips, however, when excited with light of approximately 420 nm. Therefore, excitation at approximately 420 nm with emission at approximately 464 nm is preferred for polyethylene terephthalate strips.

The container or pouch may be, but is not limited to, a trilaminate comprising an outer layer of polyethylene terephthalate, a middle layer of aluminum foil, and an inner layer of polyolefin, with a cut-out portion in the trilaminate constituting the light transmissive area or window.

As can readily be appreciated, the present invention can be applied to the quality control testing of massive quantities of food, either by incorporating the coated strip and screen into every container of food or into selected representative containers. Plastic coated strips are typically less fragile and more flexible than glass coated strips and, therefore, may be preferable for mass production and/or for transportation and storage. The present invention is amenable to testing under a wide spectrum of conditions, e.g., in the laboratory using sophisticated light sources and fluorescence spectroscopy equipment, in the field using a hand-held lamp and the naked eye or, possibly, by remote sensing using fiber optics.

One particularly advantageous aspect of the present technique is that it can be conducted either at room temperature or at elevated temperatures.

Additional objects, features and advantages of the invention will be set forth in pan in the description which follows, and in part will be obvious from the description or may be learned by practice of the invention. The objects of the invention also may be realized and attained by means of instrumentalities and combinations not particularly pointed out in the description which follows but set forth in the appended claims.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In the drawings wherein like reference numerals represent like parts.

DETAILED DESCRIPTION OF PREFERRED EMBODIMENTS

Figure 1:
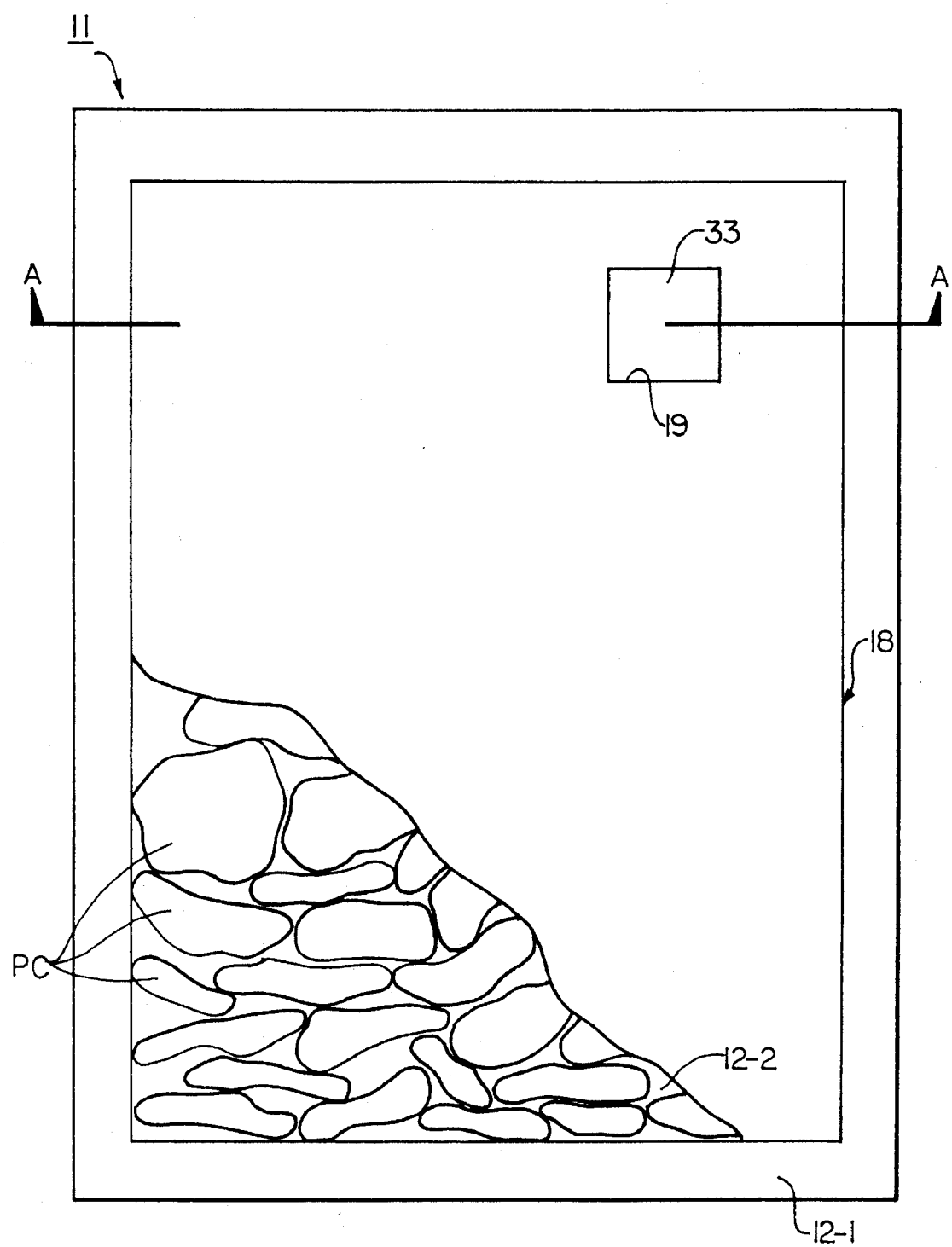
FIG. 1 is a front view of one embodiment of a dry or intermediate moisture food-containing package assembly constructed according to the teachings of the present invention, the package assembly shown being broken away in part to reveal a quantity of potato chips contained therein.
Figure 2:
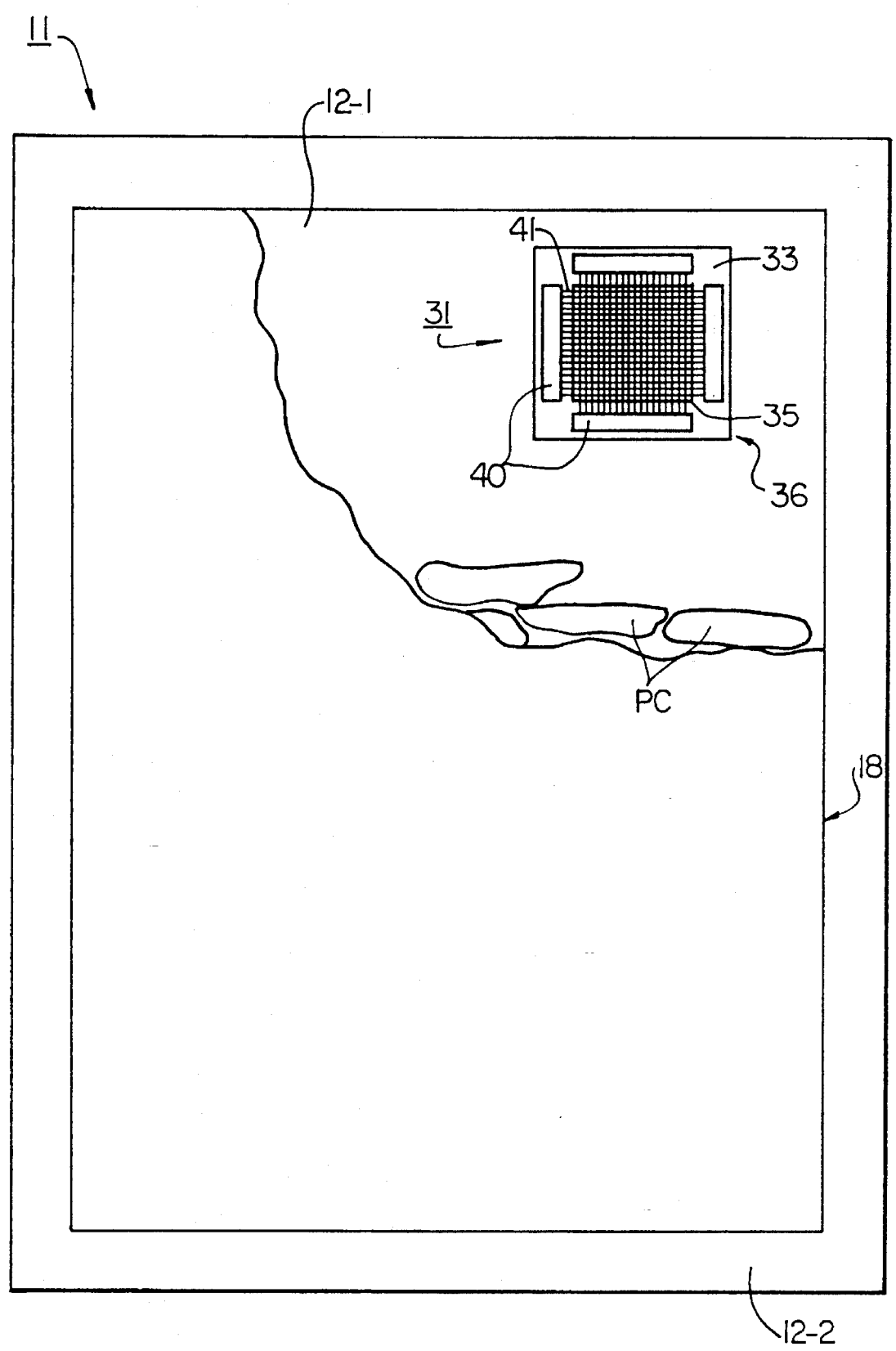
FIG. 2 is a rear view of the dry or intermediate moisture food-containing package assembly shown in FIG. 1, the package assembly being broken away in part to reveal the testing device of the present invention.
Figure 3:
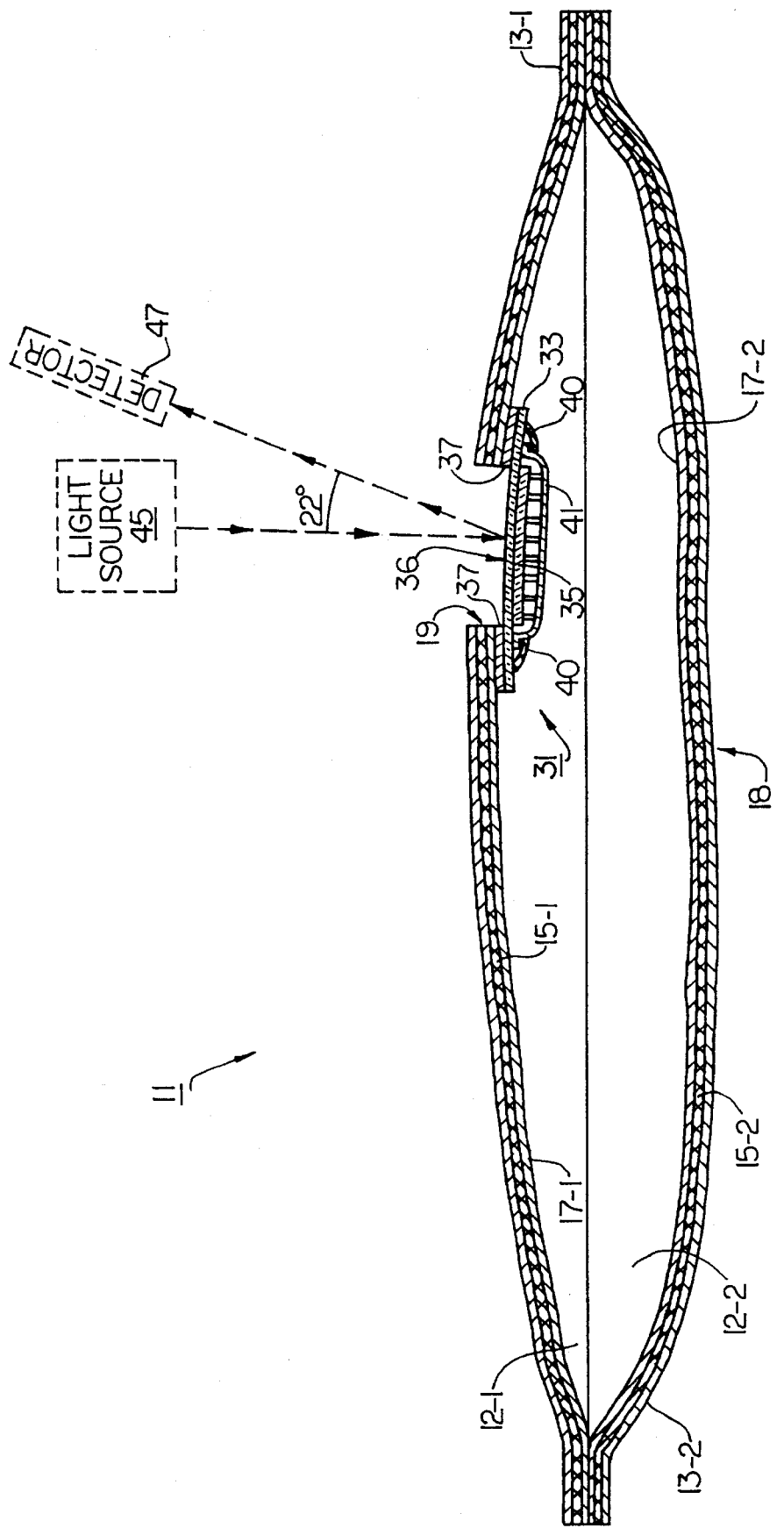
FIG. 3 is an enlarged section view of the package assembly taken along line A—A in FIG. 1.

Referring now to FIGS. 1 through 3, there are shown from, rear and enlarged section views, respectively, of a package assembly for containing dry or intermediate moisture foods, the package assembly being constructed according to the teachings of the present invention and being represented generally by reference numeral 11. Although package assembly 11 is shown in FIG. 1 being used to hold a quantity of potato chips PC, it is to be understood that other types of dry or intermediate moisture foods, other than potato chips, could be stored therein.

Package assembly 11 (FIG. 3) includes a pair of conventional trilaminate food package sheets 12-1 and 12-2, each sheet 12 being made up of an outer layer of polyethylene terephthalate 13, a middle layer of aluminum foil 15 and an inner layer of polyolefin 17.

In FIG. 3 the respective layers of the trilaminate food package sheets 12-1 and 12-2 have been labeled with the numerical suffix corresponding to the sheet of which it comprises a part; in this manner, the layers for sheet 12-1 are labeled 13-1, 15-1 and 17-1 while the respective layers for sheet 12-2 are labeled 13-2, 15-2 and 17-2. Sheets 12-1 and 12-2 are heat-sealed to one another along their respective peripheries to form a container or pouch 18 for holding food. A light transmissive window or area 19 having a size of approximately 2 mm×2 mm is cut out of sheet 12-1 for reasons to be discussed below.

Package assembly 11 also includes a device 31 for testing the oxidative status of foods contained within pouch 18. In the embodiment shown, device 31 includes a 3 mm×3 mm strip of polyethylene terephthalate 33 having a polyamide coating 35 deposited on one side thereof. Polyamide coating 35 is preferably scraped off or otherwise removed from the periphery of strip 33 so that it is confined to a central area of about 2 mm×2 mm area on strip 33. The combination of plastic strip 33 and polyamide coating 35 (collectively represented herein by reference numeral 36) is manufactured by Macherey-Nagel and Co. (Düren, Germany) and is commercially available from Brinkmann Instruments, Inc. (Westbury, N.Y.) under the name of Polygram Polyamide-6 UV for Thin Layer Chromatography. Strip 33 is fixed to inner layer 17-1 of sheet 12-1 using room temperature vulcanized (RTV) adhesive 37 (Silicone Contractors, General Electric Co., Waterford, N.Y.) and appropriately positioned relative to window 19 so that polyamide coating 35 is aligned with window 19 and faces in towards pouch 18.

Device 31 also includes an aluminum wire screen 41 which surrounds the underside of coating 35 and which extends a short distance (about 2 mm) into pouch 18. Screen 41, which is used to prevent potato chips PC and other materials within pouch 18 from coming into contact with coating 35, is fixed to strip 33 with Kalt Silver Mylar tape 40 (Kalt Co.). Screen 41 may be cut and bent into the appropriate size and shape from conventional aluminum screening materials (e.g., 20 wires/inch aluminum screening).

Although not used in the present embodiment, one or more O-rings (Viton, Thomas Scientific Co.) or similar spacers could be positioned between coating 35 and screen 41 to provide structural support to screen 41.

So that device 31 can later be used to accurately test the oxidative status of potato chips PC, one must ensure that at least some of the potato chips PC are stored within about 2 cm of polyamide coating 35. Obviously, if the potato chips, once settled in pouch 18, are within 2 cm of polyamide coating 35, nothing further need be done. Where, however, after settling, the potato chips PC are not sufficiently close to polyamide coating 35, package assembly 11 must be shaken, inverted or otherwise agitated soon after packaging so that at least some potato chips PC are stored within about 2 cm of polyamide coating 35. The aforementioned 2 cm distance is very important since the present inventor has discovered that the fluorogenic volatile compound present in food lipids has a very short effective fluorogenic distance (i.e., about 2 cm) and half-life.

To then test the oxidative status of potato chips PC within pouch 18, polyamide coating 35 is illuminated through window 19 and strip 33 using an external light source 45. Light source 45 preferably emits light at a wavelength of about 420 nm so as not to excite residual fluorophors present in polyethylene terephthalate. The resultant fluorescence from polyamide coating 35 is then detected at 464 nm using an externally placed light detector 47. As seen in FIG. 3, the angle of incidence of the exciting light is preferably normal to strip 33 and the angle of observation of the fluorescent light is preferably a shallow angle, such as 22 degrees relative to the normal. Such an arrangement minimizes variability often encountered in front-face, solid-sample fluorometry.

Figure 4:
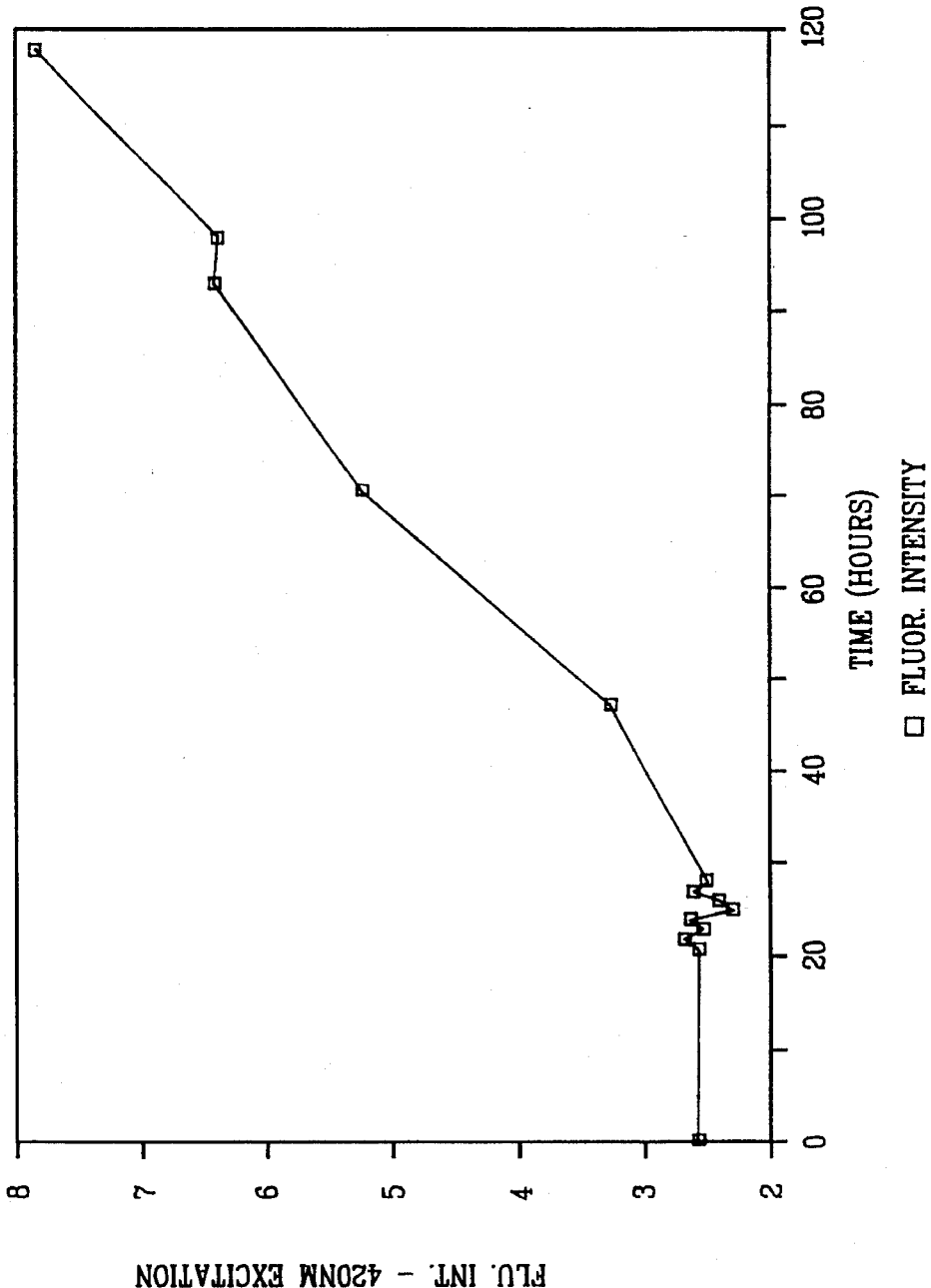
FIG. 4 is a graph depicting fluorescence intensity as a function of time at room temperature for a potato chip-containing package assembly of the type shown in FIG. 1, the fluorescence intensity measurements being obtained in accordance with the method of the present invention.
Figure 5:
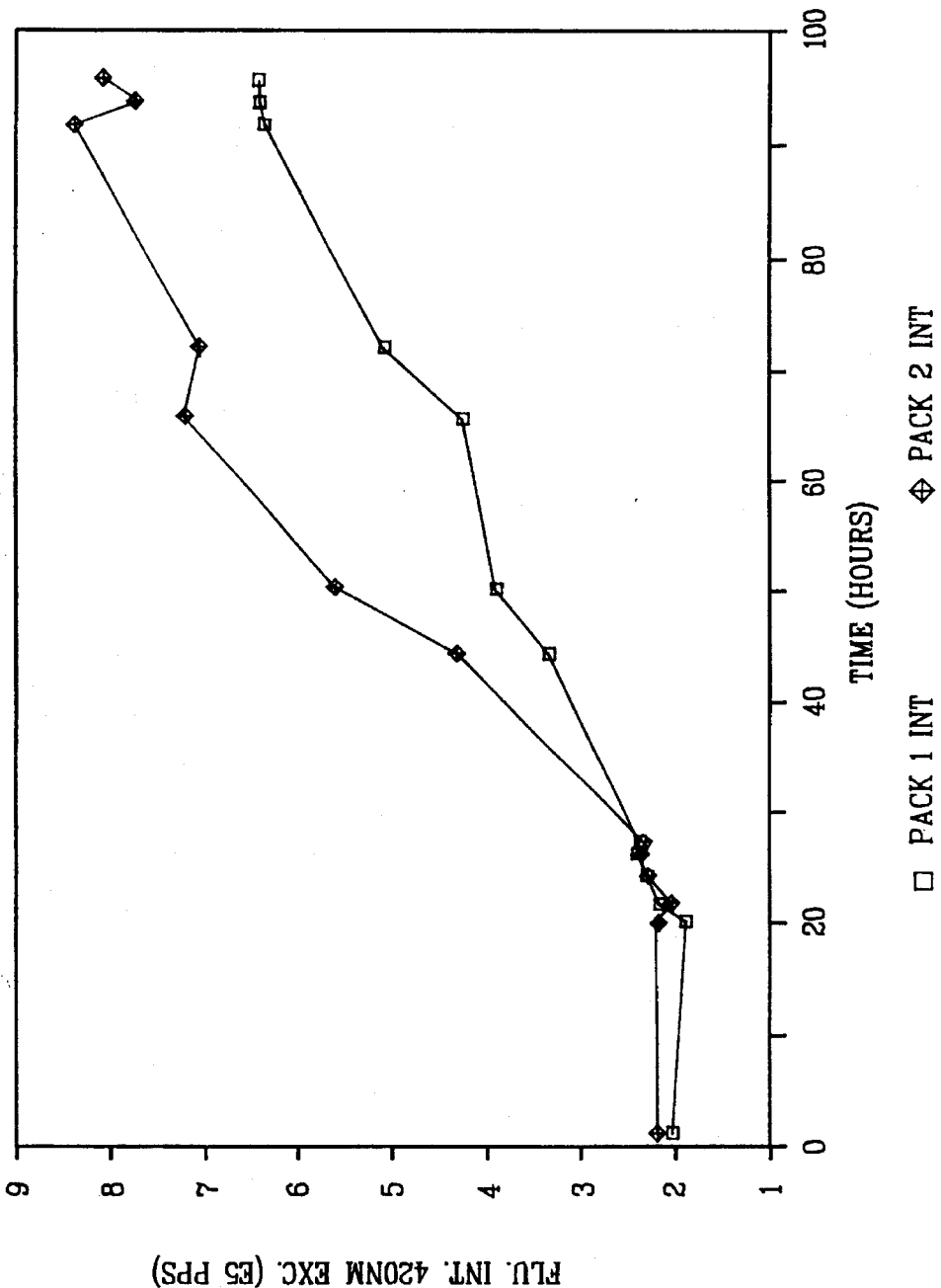
FIG. 5 is a graph depicting fluorescence intensity as a function of time at room temperature for a pair of potato chip-containing package assemblies of the type shown in FIG. 1, the fluorescence intensity measurements being obtained in accordance with the method of the present invention.

EXAMPLE I 1 oz. quantities of 'TAYTERS™ Natural Flavor Potato Chips were thoroughly dusted with corresponding 1 g quantities of $CoCl_2.6H_2O$, an oxidation accelerant, and separately packaged in package assemblies 11. The assemblies were continuously inverted for 3 minutes, dark-stored at room temperature, and the above-described testing method was performed. The resulting fluorescence measurements taken over time are shown in FIGS. 4 and 5.

EXAMPLE II

Figure 6:
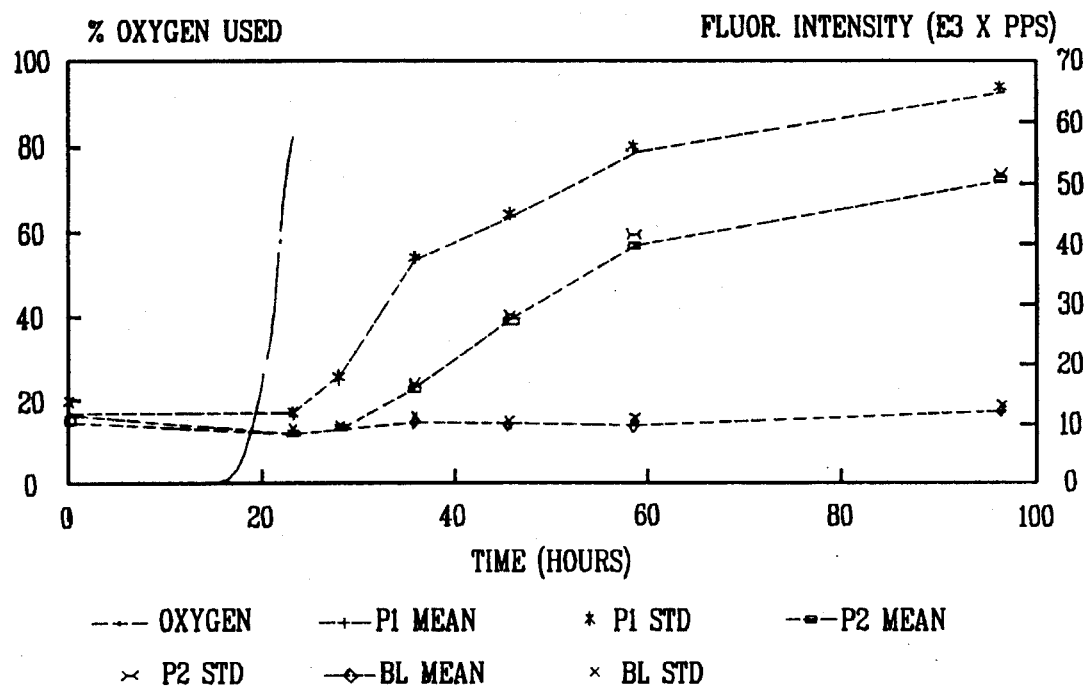
FIG. 6 is a graph depicting oxygen uptake and fluorescence intensity as a function of time at room temperature for three package assemblies, two of which contain potato chips and one of which is empty, the three package assemblies differing from the package assembly of FIG. 1 in that a glass strip, instead of a plastic strip, is used to hold the polyamide coating, the fluorescence intensity measurements being obtained in accordance with the method of the present invention.
Figure 7:
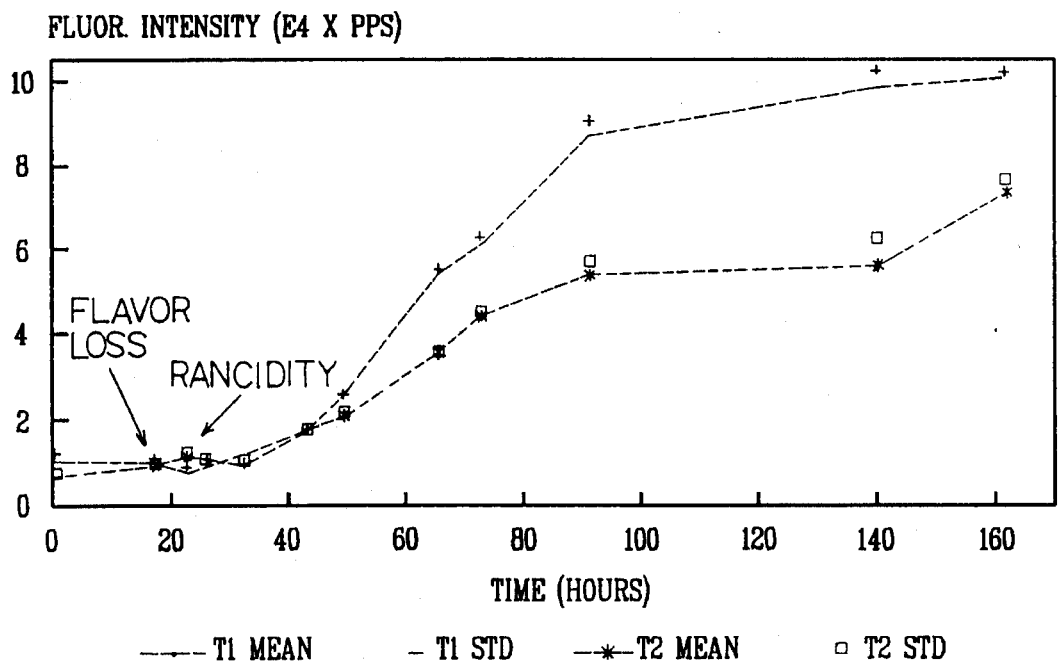
FIG. 7 is a graph depicting odor development and fluorescence intensity as a function of time at room temperature for a pair of potato chip-containing package assemblies of the type used in FIG. 6, the fluorescence intensity measurements being obtained in accordance with the method of the present invention.

The same conditions described above in Example I were replicated with the exception that the polyamide-coated plastic strip 36 was replaced with a polyamide-coated glass strip of the type commercially available from Schleicher and Schuell, Inc. (Keene, N.H.) as Polyamide UV indicator No. G1600/LS 254). The resulting fluorescence measurements taken over time for a pair of such package assemblies containing potato chips P1 and P2 and an empty package assembly BL are shown in FIGS. 6 and 7. FIG. 6 additionally shows oxygen uptake within one of the package assemblies, and FIG. 7 additionally shows organoleptic assessment of rancidity development by three independent observers.

The following observations can be made based on the results in FIGS. 4 through 7: (1) cobalt-accelerated oxidizing potato chips at room temperature produce polyamide fluorescence within 24 hours; (2) oxygen uptake begins at 18 hours; (3) initial fluorescence development is quasi-linear; (4) measurements have good reproducibility and sensitivity, with a low standard deviation of readings taken at different locations on the glass or plastic surface; and (5) rancidity is detectable at 22 hours and flavor loss is detectable at 19 hours.

The embodiments of the present invention described above are intended to be merely exemplary and those skilled in the art shall be able to make numerous variations and modifications to it without departing from the spirit of the present invention. For example, container 18 could be made from, comprise or consist of a metal can, a glass jar, a single layer of plastic, or the like. All such variations and modifications are intended to be within the scope of the present invention as defined in the appended claims.

What is claimed is:

1. A method of rapid, dry, non-invasive, non-destructive external monitoring of the oxidative status of packaged lipid-containing dry or intermediate moisture foods stored at ambient temperatures, to enable shelf-life prediction and failed item removal, the method comprising the steps of:
   a) providing a package assembly, said package assembly comprising:
      (i) a container within which the lipid-containing dry or intermediate moisture foods are stored, said container being provided with a light transmissive window, and
      (ii) a device comprising
         (A) a transparent plastic strip positioned across the light transmissive window, said transparent plastic strip having a first side facing in towards the interior of said container and a second side facing outward through the light transmissive window, and
         (b) a polyamide coating deposited on said first side of said transparent plastic strip;
   b) placing lipid-containing dry or intermediate moisture foods within said container within about 2 cm of said polyamide coating during oxidation of lipids in the foods to produce compounds that induce fluorescence therein when excited with light of an appropriate excitation wavelength;
   c) illuminating said polyamide coating from outside the container through said transparent plastic strip so that the illumination strikes the second side of the transparent plastic strip first, with light having an excitation wavelength of about 420 nm; and
   d) observing the resultant fluorescence at about 464 nm wavelength from said polyamide coating through said transparent plastic strip.

2. The method as claimed in claim 1 wherein said container is made from at least one sheet of sealed material.

3. The method as claimed in claim 1 wherein said transparent plastic strip is made of polyethylene terephthalate.

4. The method as claimed in claim 3 wherein said appropriate excitation wavelength is about 420 nm and said appropriate emission wavelength is about 464 nm.

5. The method as claimed in claim 4 wherein the polyamide coating is comprised of polymerized epsilon-caprolactam.

6. The method as claimed in claim 1 wherein said illuminating step comprises illuminating said polyamide coating from outside the container with a beam of light having a wavelength of about 420 nm normal to said transparent plastic strip and wherein said observing step comprises observing the resultant fluorescence at a wavelength of about 464 nm.

7. The method as claimed in claim 1 wherein one or more of said placing, illuminating and observing steps are performed at room temperature.

8. The method as claimed in claim 1 wherein said placing, illuminating and observing steps are performed at room temperature.

9. A method of rapid, dry, non-invasive, non-destructive external monitoring of the oxidative status of packaged lipid-containing dry or intermediate moisture foods stored at ambient temperatures, to enable shelf-life prediction and failed item removal, the method comprising the steps of:
   a) providing a package assembly, said package assembly comprising:
      (i) a container within which the lipid-containing dry or intermediate moisture foods are stored, said container being provided with a light transmissive window, and
      (ii) a device comprising
         (a) a transparent glass strip positioned across the light transmissive window, said transparent glass strip having a first side facing in towards the interior of said container, and
         (b) a polyamide coating deposited on said first side of said transparent glass strip;

b) storing the lipid-containing dry or intermediate moisture foods within said container in sufficient proximity to said polyamide coating to produce compounds that induce fluorescence therein when excited with light of about 420 nm wavelength;

c) illuminating said polyamide coating through said transparent glass strip with light of about 420 nm wavelength; and d) observing the resultant fluorescence from said polyamide coating through said transparent glass strip at about 464 nm emission wavelength.

10. The method as claimed in claim 9 wherein the polyamide coating is comprised of polymerized epsilon-caprolactam.

* * * * *